(12) United States Patent
Haaland et al.

(10) Patent No.: US 7,863,484 B1
(45) Date of Patent: Jan. 4, 2011

(54) METHOD FOR REDUCING AMINOISOPHTHALIC ACID BISAMIDE RELATED IMPURITIES IN PREPARATION OF NON-IONIC X-RAY CONTRAST AGENTS

(75) Inventors: Torfinn Haaland, Spangereid (NO); Ole Magne Homestad, Spangereid (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 12/571,457

(22) Filed: Oct. 1, 2009

Related U.S. Application Data

(60) Provisional application No. 61/227,086, filed on Jul. 21, 2009.

(51) Int. Cl.
*C07C 233/65* (2006.01)
(52) U.S. Cl. .................................. 564/153; 424/9.452
(58) Field of Classification Search ................. 564/153; 424/9.452
See application file for complete search history.

(56) References Cited

U.S. PATENT DOCUMENTS

| 6,274,762 B1 | 8/2001 | Malthe-Sorenssen et al. |
| 6,441,235 B1 | 8/2002 | Parady et al. |
| RE38,856 E | 10/2005 | Thielking et al. |
| 2002/0095053 A1 | 7/2002 | Parady et al. |
| 2004/0082811 A1 | 4/2004 | Anelli et al. |

FOREIGN PATENT DOCUMENTS

| WO | 00/29372 | 5/2000 |

*Primary Examiner*—Shailendra Kumar

(57) ABSTRACT

This invention relates generally to the preparation of non-ionic X-ray contrast agents, iohexyl, ioversol, and iodixanol. It further relates to a method for improving the purity of 5-amino-N,N'-bis(2,3-dihydroxypropyl)-isophthalamide (or ABA), an intermediate in the industrial preparation of these non-ionic X-ray contrast agents. In particular, it relates to a method for significantly removing ABA monomethylester and ABA dimer from ABA by hydrolyzing ABA under a pH between about 12 to about 13 in an aqueous medium to convert ABA monomethylester to ABA monoacid, before the iodination reaction of ABA.

1 Claim, No Drawings

METHOD FOR REDUCING AMINOISOPHTHALIC ACID BISAMIDE RELATED IMPURITIES IN PREPARATION OF NON-IONIC X-RAY CONTRAST AGENTS

CROSS REFERENCE TO RELATED APPLICATIONS

The present application claims benefit of priority under 35 U.S.C. §119(e) to U.S. Provisional Application No. 61/227,086 filed Jul. 21, 2009, the entire disclosure of which is hereby incorporated by reference.

TECHNICAL FIELD

This invention relates generally to the preparation of non-ionic X-ray contrast agents. It further relates to a method for improving the purity of 5-amino-N,N'-bis(2,3-dihydroxypropyl)-isophthalamide (or ABA), an intermediate in the industrial preparation of non-ionic X-ray contrast agents. In particular, it relates to a method for significantly removing ABA monomethylester and ABA dimer from ABA prior to its iodination.

BACKGROUND OF THE INVENTION

Non-ionic X-ray contrast agents constitute a very important class of pharmaceutical compounds produced in large quantities 5-[N-(2,3-dihydroxypropyl)-acetamido]-N,N'-bis(2,3-dihydroxypropyl)-2,4,6-triiodo-isophthalamide ("iohexyl"), N,N'-Bis(2,3-dihydroxypropyl)-5-[(2-hydroxyacetyl)-(2-hydroxyethyl)amino]-2,4,6-triiodo-benzene-1,3-dicarboxamide ("ioversol"), and 1,3-bis(acetamido)-N,N-bis[3,5-bis(2,3-dihydroxypropyl-aminocarbonyl)-2,4,6-triiodophenyl]-2-hydroxypropane ("iodixanol") are important examples of such compounds. They contain one or two triiodinated benzene rings.

The industrial production of iohexyl, ioversol, and iodixanol involves a multistep chemical synthesis. The final drug substance must meet the stringent purity standards set forth by regulatory agencies. While purity is of the utmost importance, it is also important to reduce the cost of production by optimizing each synthetic step. Even a small improvement in reaction design can lead to significant savings in a large scale production.

The instant improvement is directed to 5-amino-N,N'-bis(2,3-dihydroxypropyl)-isophthalamide (also known as aminoisophthalic acid bisamide, AIPA bisamid or ABA). ABA is a common intermediate in the industrial preparation of iodixanol and iohexyl. For example, one of the typical synthetic steps in preparing iodixanol is the iodination of ABA using iodine chloride to convert ABA to 5-amino-N,N'-bis(2,3-dihydroxypropyl)-2,4,6-triiodoisophthalamide (Compound B). See Scheme 1; see also U.S. Pat. Nos. 6,441,235 and 6,274,762. This instant invention is directed to removing substantial amounts of impurities in ABA before its iodination reaction.

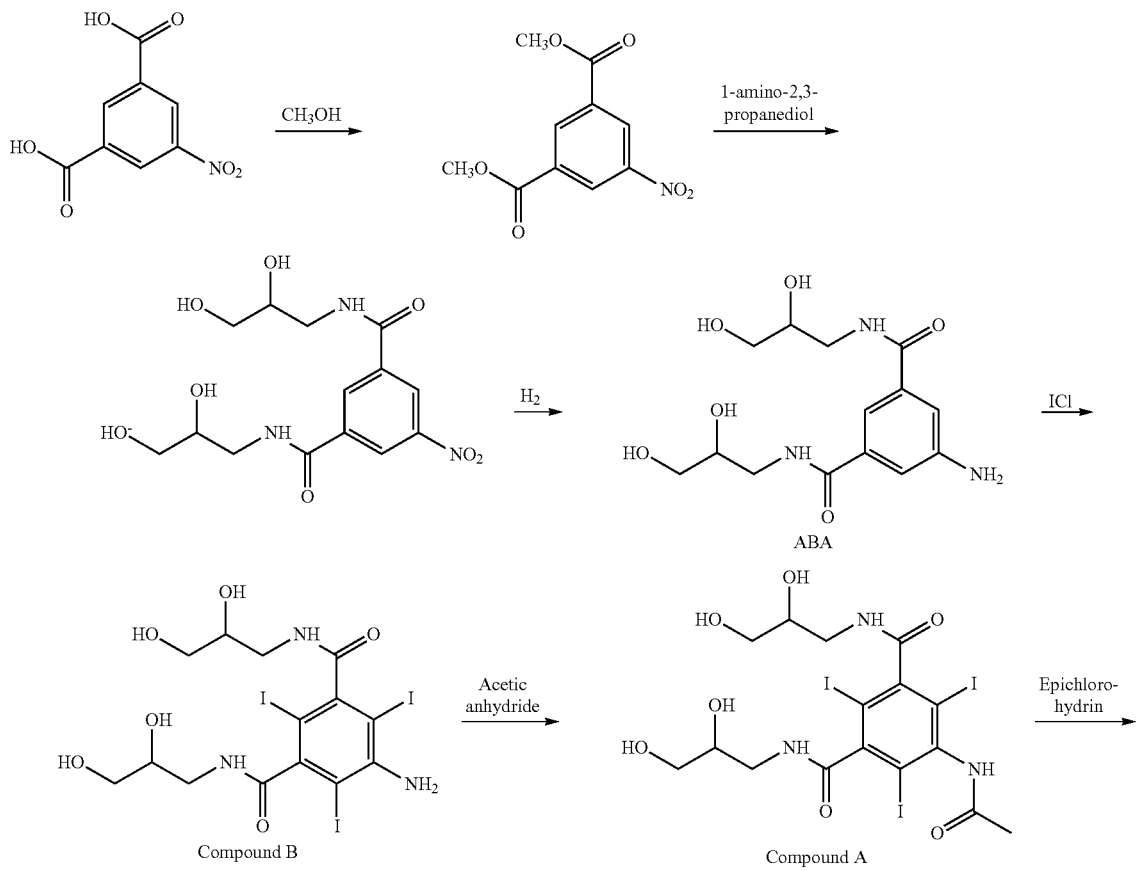

Scheme 1

-continued

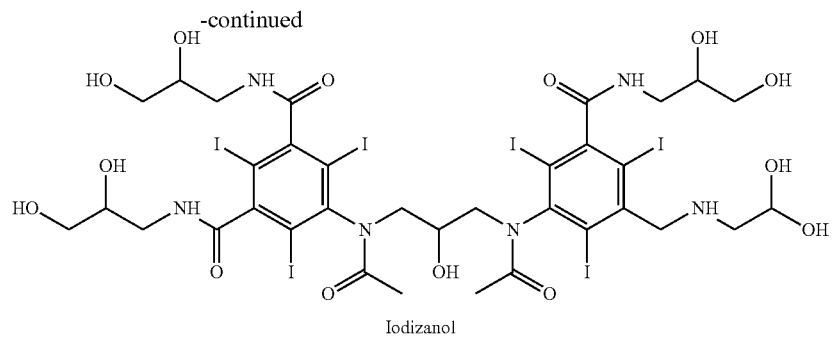
Iodizanol

SUMMARY OF THE INVENTION

The present invention provides a process for eliminating two common impurities in ABA, ABA monomethylester and ABA dimer, prior to the iodination reaction of ABA in an industrial scale synthesis of iohexyl, ioversol, and iodixanol. Specifically, the process is directed to hydrolyzing ABA under a pH between about 12 to about 13 in aqueous medium to convert ABA monomethylester to ABA monoacid. After the instant process, ABA is substantially free of ABA monomethylester and ABA dimer, which greatly simplifies the subsequent purification processes.

DETAILED DESCRIPTION OF THE INVENTION

ABA may be in its free form or as a hydrochloride as the starting material for iodination in the synthesis of iodixanol and iohexyl. Three common impurities of ABA are ABA monomethylester, ABA dimer, and ABA monoacid, as shown below:

These impurities can be iodinated along with ABA itself. Among them, iodinated ABA monoacid is relatively easy to remove in later purification steps. But we have found that triiodinated ABA monomethylester and iodinated ABA dimer are extremely difficult to remove in subsequent purification steps. For example, triiodinated ABA monomethylester is remarkably stable at virtually all pHs, and it is difficult to remove in the subsequent crystallization steps.

Because iohexyl, ioversol, and iodixanol all have strict regulatory specifications with regard to impurity profile, it is important to limit the amount of related iodinated impurities to a minimum. Extensive purification steps (including recrystallization) at later stages in the synthesis are required if the initial levels of ABA monomethylester and ABA dimer are not reduced. However, additional purification steps would increase the cost of production or lower the production yield due to loss of intermediates or final drug substance as a result of new purification procedures at later stages of synthesis.

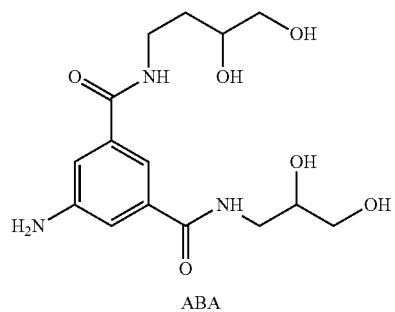
ABA

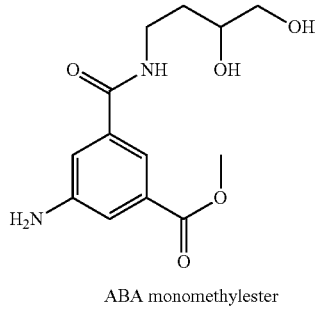
ABA monomethylester

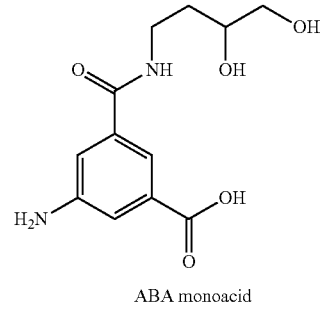
ABA monoacid

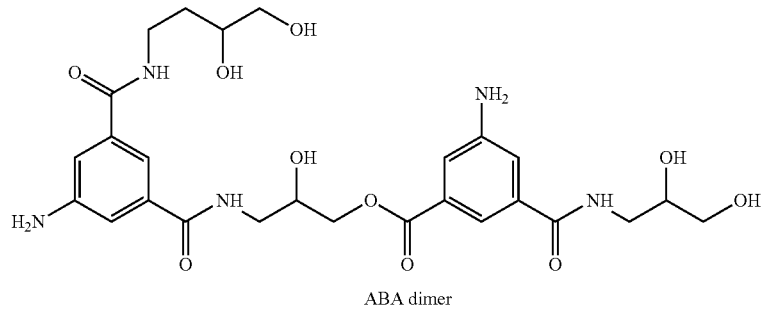
ABA dimer

We have found that the level of ABA monomethylester can be reduced in an efficient manner by basic hydrolysis. The hydrolysis is carried out in an aqueous reaction medium, which includes a medium containing a mixture of water and another solvent. The reaction product from the hydrolysis is ABA monoacid, which is readily removable in the crystallization of both ABA and the subsequent triiodinated products. In addition, ABA dimer is simultaneously removed from ABA in the same hydrolysis process. Because of the early removal of these impurities from ABA, yields of all subsequent steps are improved. For example, the purity of Compound B and hence Compound A increases and, in turn, the dimerisation from Compound A to iodixanol becomes more efficient.

The hydrolysis of the instant invention is performed at a pH of about 12 to about 13. We have found that this pH range gives a suitable hydrolysis rate and at the same time prevents hydrolysis of the amide side chains in ABA. The reaction may be complete in less than 1 hour, preferably less than 15-20 minutes or even more within one minute. The reaction is typically run at room temperature, e.g., 20-25° C. The levels of ABA monomethylester and ABA dimer may reach zero after the reaction. Typically, ABA monomethylester may be reduced from about 0.4 to about 0.7% to less than about 0.04% as observed in HPLC and ABA dimer from about 0.1% to less than about 0.01%. The amount of ABA monoacid is typically increased from about 0.2-0.3% to about 0.6-0.8% in the reaction based on HPLC analysis.

The invention is illustrated further by the following examples that are not to be construed as limiting the invention in scope to the specific procedures described in them.

EXAMPLES

Example 1

To an aqueous solution of ABA (200 mL, 38.8 w/w %) at pH 2.0 was added an aqueous solution of sodium hydroxide (50 w/w %, 11 mL) over 20 minutes at room temperature. A pH of 13.0 was observed. An immediate HPLC analysis showed that the amount of ABA monomethylester had been reduced from 0.34 to 0.09%. The amount of ABA dimer had not been changed. After 10 minutes at pH 13.0 HPLC showed that the ABA monomethylester had been further reduced to 0.00% and the ABA dimer from 0.04 to 0.02%. Adjustment of pH to 3.0 by hydrochloric acid (17.5 w/w %, 18 mL) over 15 minutes gave no changes in the impurity profile.

Example 2

To an aqueous solution of ABA (200 mL, 38.8 w/w %) at pH 2.0 was added an aqueous solution of sodium hydroxide (50 w/w %, 16 mL) over 20 minutes at room temperature. A pH of 13.0 was observed. An immediate HPLC analysis showed that the amount of ABA monomethylester had been reduced from 0.34 to 0.00% and the ABA dimer from 0.04 to 0.00%. The amount of ABA monoacid had increased from 0.16 to 0.47%. After 10 minutes at pH 13.0 HPLC showed no changes in the impurity profile except an increase in ABA monoacid content from 0.47 to 0.54%. Adjustment of pH to 3.3 by hydrochloric acid (17.5 w/w %, 34 mL) over 15 minutes gave no further changes in the impurity profile.

Example 3

To an aqueous solution of ABA (100 mL, 38.8 w/w %) at pH 2.0 was added an aqueous solution of sodium hydroxide (50 w/w %, 8 mL) over 2 minutes at room temperature. A pH of 13.0 was observed. An immediate HPLC analysis showed that the amount of ABA monomethylester had been reduced from 0.34 to 0.00% and the ABA dimer from 0.04 to 0.00%. The amount of ABA monoacid had increased from 0.16 to 0.52%. After 10 minutes at pH 13.0 HPLC showed no changes in the impurity profile. Adjustment of pH to 3.0 by hydrochloric acid (17.5 w/w %, 17 mL) over 2 minutes gave no changes in the impurity profile.

Example 4

To an aqueous solution of ABA-HCl (pH about 0) is added an aqueous solution of sodium hydroxide (50 w/w %) to a pH of 12.5-13.0 over 15-30 minutes at 20-25° C. The ABA-monomethylester content is reduced from about 0.4% to less than 0.01% and the ABA dimer content from about 0.1% to less than 0.01%. Adjustment of pH to 2.5-3.0 by hydrochloric acid (17.5 w/w %) over 15-60 minutes gives no changes in the impurity profile.

All patents, journal articles, publications and other documents discussed and/or cited above are hereby incorporated by reference.

We claim:

1. A process for eliminating the impurities of ABA monomethylester and of ABA dimer contained in an aqueous solution of 5-amino-N,N'-bis(2,3-dihydroxypropyl)-isophthalamide (ABA) or ABA hydrochloride by hydrolyzing said impurities in said aqueous solution at a pH between about 12 to about 13 by the addition of sodium hydroxide.

* * * * *

UNITED STATES PATENT AND TRADEMARK OFFICE
CERTIFICATE OF CORRECTION

PATENT NO. : 7,863,484 B1
APPLICATION NO. : 12/571457
DATED : January 4, 2011
INVENTOR(S) : Torfinn Haaland and Ole Magne Homestad It is certified that error appears in the above-identified patent and that said Letters Patent is hereby corrected as shown below:

Column 4, line 16, the term "Iodizanol" should read as --Iodixanol--.

The structures found at the bottom of Columns 3 and 4 should appear as follows:

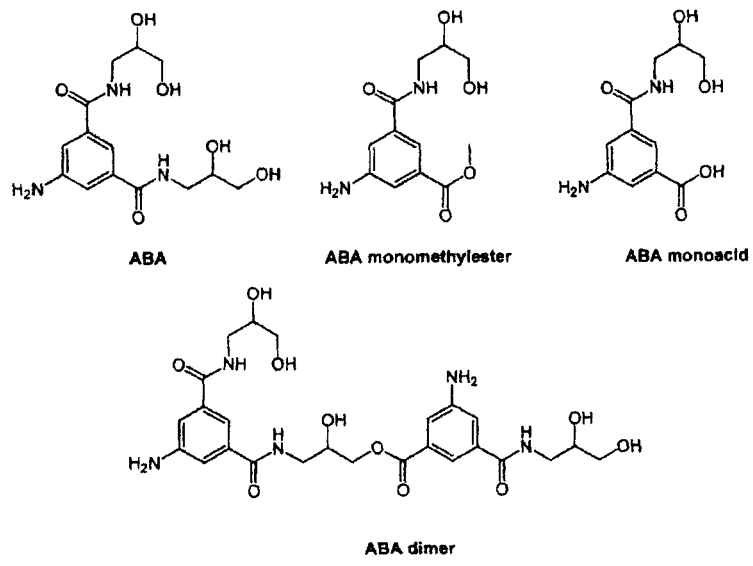

-- --.

Signed and Sealed this
Thirteenth Day of September, 2011

David J. Kappos
*Director of the United States Patent and Trademark Office*